United States Patent [19]

Ban et al.

[11] Patent Number: 4,712,003
[45] Date of Patent: Dec. 8, 1987

[54] BLIND PERSON GUIDE DEVICE

[76] Inventors: Itsuki Ban, 3-50-18 Higashi-Oizumi; Yuji Mitsuta, 4-28-17 Shimoshakujii, both of Nerima-ku, Tokyo, Japan

[21] Appl. No.: 18,740

[22] Filed: Feb. 24, 1987

Related U.S. Application Data

[63] Continuation of Ser. No. 632,668, Jul. 20, 1984, abandoned.

[30] Foreign Application Priority Data

Jul. 27, 1983 [JP] Japan ............................ 58-115612[U]
Jun. 6, 1984 [JP] Japan .............................. 59-82961[U]

[51] Int. Cl.4 ............................................. G01S 17/06
[52] U.S. Cl. .................................... 250/221; 250/215; 340/555; 342/24
[58] Field of Search ...................... 250/221, 222.1, 215; 340/556, 557, 555; 342/24

[56] References Cited

U.S. PATENT DOCUMENTS

| | | | |
|---|---|---|---|
| 3,546,467 | 12/1970 | Benjamin | 343/5 BL |
| 3,718,896 | 2/1973 | Mowat | 343/5 BL |
| 4,280,204 | 7/1981 | Elchinger | 343/5 BL |
| 4,356,393 | 10/1982 | Fayfield | 250/227 |
| 4,459,476 | 7/1984 | Weissmueller et al. | 250/221 |
| 4,591,710 | 5/1986 | Komadina et al. | 250/221 |

*Primary Examiner*—Edward P. Westin
*Assistant Examiner*—Charles Wieland
*Attorney, Agent, or Firm*—George A. Loud

[57] ABSTRACT

There is disclosed a blind person guide device comprising a walking stick, a source mounted on a front face of the walking stick for emitting a beam of infrared radiation in a forward direction, a photoelectric element mounted on the front face of the walking stick for receiving infrared radiation reflected from an object irradiated by the beam, an electric circuit for producing information as to a distance to the object based on the illuminance or energy of received radiation on the photoelectric element, an oscillator for generating electric vibrations having a frequency and an amplitude which are dependent on the distance information produced by the electric circuit, and a vibrator vibratable in response to the electric vibrations and having a vibrating surface against which a human skin can be pressed.

5 Claims, 16 Drawing Figures

BLIND PERSON GUIDE DEVICE

This is a continuation of Ser. No. 632,668, filed 7-20-84 now abandoned.

BACKGROUND OF THE INVENTION

The present invention relates to a blind person guide device, and more particularly to a guide device having an infrared range finder or sonar for giving distance information to a blind person to help the blind person in walking safely.

Blind persons use walking sticks as an aid for walking safely. The walking stick gives the blind person direct information on dangerous objects existing in a range that can be reached by the walking stick. The walking stick also gives indirect information about the position of a nearby obstacle based on the echo of a click generated when it hits a hard ground, the echo being reflected from a relatively large object such as a wall positioned in a short distance from the blind person. An experiment indicates that a blind person with a walking stick can recognize a screen in a long hallway at a distance of 2 m from the screen. The principle is the same as ultrasonic echo sounding utilized by bats and dolphins. The source of sound for blind persons can be a footstep or a rustling sound of the clothes in addition to the walking stick.

However, if an object is small or positioned at a distance, then it is difficult to get correct information of the object with such an echo sounding principle. Desired distance information cannot be gained unless some aids such as a sonar or a range finder is used. Various means for measuring the distance to an object have been known. Some rely on electromagnetic or ultrasonic radiation to measure a distance based on a time required for the wave to reach an object, a wave interference, or triangulation. The known ranging devices are large in size and expensive, and need a highly accurate mechanism. The ultrasonic range finder is particularly disadvantageous in that since ultrasonic radiation spreads in a wide angle, information on a bearing is difficult to obtain and the distance up to a small object cannot be measured.

There is known as a walking aid for blind persons a device for enabling the blind person to recognize an object as a sound image. More specifically, the device operates by applying a signal from a range finder to a voltage-controlled oscillator and a voltage-controlled amplifier which produces a sound dependent on the distance to an object through an earphone. The person using this device can find a distance by recognizing an intensity of the sound, or a pitch of the sound, or both.

Blind persons have a very sharp sense of hearing. Therefore, wearing an earphone even on one ear would interfere with the normal activity to listen to ambient direct sounds. There has also been proposed to incorporate a sonar and a loudspeaker in a walking stick so that a sonar sound will be generated by the loudspeaker. While sounds from the loudspeaker can easily be heard in a room, they cannot clearly be heard unless they are louder in an open space. The sound from the loudspeaker in the walking stick has the advantages of attracting the attention of other people, but some blind persons do not want to attract too much attention. The blind also have a sharp sense of touch as indicated by the fact that they can read braille points by their fingertip.

Ultrasonic ranging devices include a device for varying the sound frequency dependent on the distance to an obstacle or a device having a plurality of ultrasonic transducers for producing a sound image indicative of the distance and bearing of an obstacle based on the localization of a sound source as perceived by the sense of hearing. With these ultrasonic devices, information is transmitted aurally to blind persons, and ambient sounds are masked so that the amount of information carried by the ambient sounds is reduced. Therefore, the total amount of information perceived by a blind person is not increased. The ultrasonic ranging devices also have the problem of consuming a large current. For the reasons described above, the ultrasonic ranging devices are not suitable as walking aids. Furthermore, when blind people free themselves from the ultrasonic ranging devices, they tend to forget to turn off the power supply switch and it is not easy for them to confirm whether the power supply switch is turned off or not.

SUMMARY OF THE INVENTION

The above-described drawbacks in the prior art apparatus have been successfully eliminated by the present invention.

It is an object of the present invention to provide a blind person guide device having a sonar including a range finder which is capable of measuring a distance up to 10 m within as small an area as possible, can indicate the bearing of an object, measure the distance in a short period of time, is small in size, light, and inexpensive with no mechanically moving parts, and has a medium for allowing a blind person to perceive information through the sense of touch without interference with the ability to hear ambient sounds.

Another object of the present invention is to provide a blind person guide device having means for transmitting information from a range finder through the sense of touch or the stimulus by low-frequency vibrations, the means including a vibrator integral with a power supply pushbutton switch so that when the pushbutton switch is depressed, information in the form of vibrations will be transmitted through the switch to a fingertip of the user.

Still another object of the present invention is to provide a blind person guide device which enables a blind person to perceive the distance up to an obstacle, can save electric consumption, and prevents the user from forgetting to turn off the power supply.

According to the present invention, the above objects can be achieved by a blind person guide device comprising a walking stick, a source mounted on a front face of the walking stick for emitting a beam of infrared radiation in a forward direction, a photoelectric element mounted on the front face of the walking stick for receiving infrared radiation reflected from an object irradiated by the beam, an electric circuit for producing information as to a distance to the object based on the illuminance or energy of received radiation on the photoelectric element, an oscillator for generating electric vibrations having a frequency and an amplitude which are dependent on the distance information produced by the electric circuit, and a vibrator vibratable in response to the electric vibrations and having a vibrating surface against which a human skin can be pressed.

A modified blind person guide device comprises a source for emitting a beam of infrared radiation in a forward direction, a photoelectric element for receiving infrared radiation reflected from an object irradiated by the beam, an electric circuit for producing information as to a distance to the object based on the illuminance or energy of received radiation on the photoelectric element, an oscillator for generating electric vibrations having a frequency and an amplitude which are dependent on the distance information produced by the electric circuit, and a power supply switch for energizing and de-energizing the electric circuit and the oscillator, the power supply switch having a pressor comprising a vibrator which is vibratable in response to the electric vibrations and against which a human skin can be pressed.

These and other objects of the invention will become apparent from the following description of embodiments thereof when taken together with the drawings.

BRIEF DESCRIPTION OF THE DRAWINGS

FIGS. 12 and 13 are perspective and cross-sectional views of the construction of the range finder of FIG. 10.

DESCRIPTION OF THE PREFERRED EMBODIMENTS

The principles of a range finder of a sonar for blind persons according to the present invention will be described.

The first principle is that when a beam of electromagnetic radiation is emitted toward an object, the luminance of the beam is prevented from being reduced, and after the beam has been emitted toward the object, the beam generally becomes scattered light so that the intensity or energy, that is, an integrated value, of the reflected electromagnetic radiation is received as a quantity proportional to the square of a distance that the radiation has travelled, thus producing distance-dependent information.

The second principle is as follows: Electromagnetic waves reflected from an object have different reflectivities within a visible region. However, electromagnetic radiation outside of the visible region has a substantially constant reflectivity. By using a light-emitting diode having a wavelength of about 1 microns to emit infrared radiation, distances can be measured on the basis of the above first principle. An infrared laser beam can also be utilized.

Distance measuring devices or range finders constructed on the above principles will hereinafter be described in detail.

Figure 1:
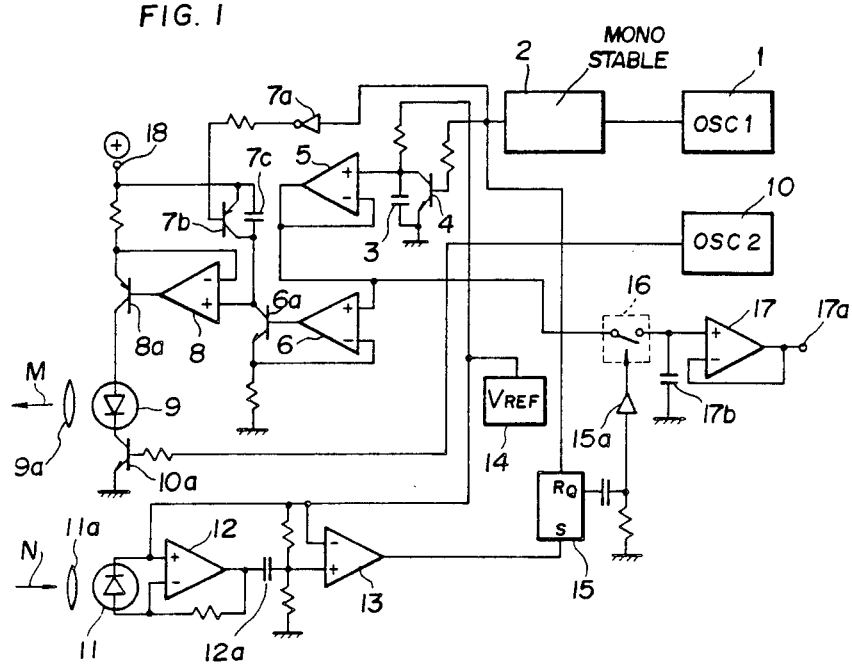
FIG. 1 is a circuit diagram of a range finder according to the present invention.

A range finder shown in FIG. 1 detects the illuminance of reflected and received light as distance information. The range finder has an osilator 1 and a monostable multivibrator 2, and their outputs are indicated by A and B, respectively, in FIG. 2.

Figure 2:
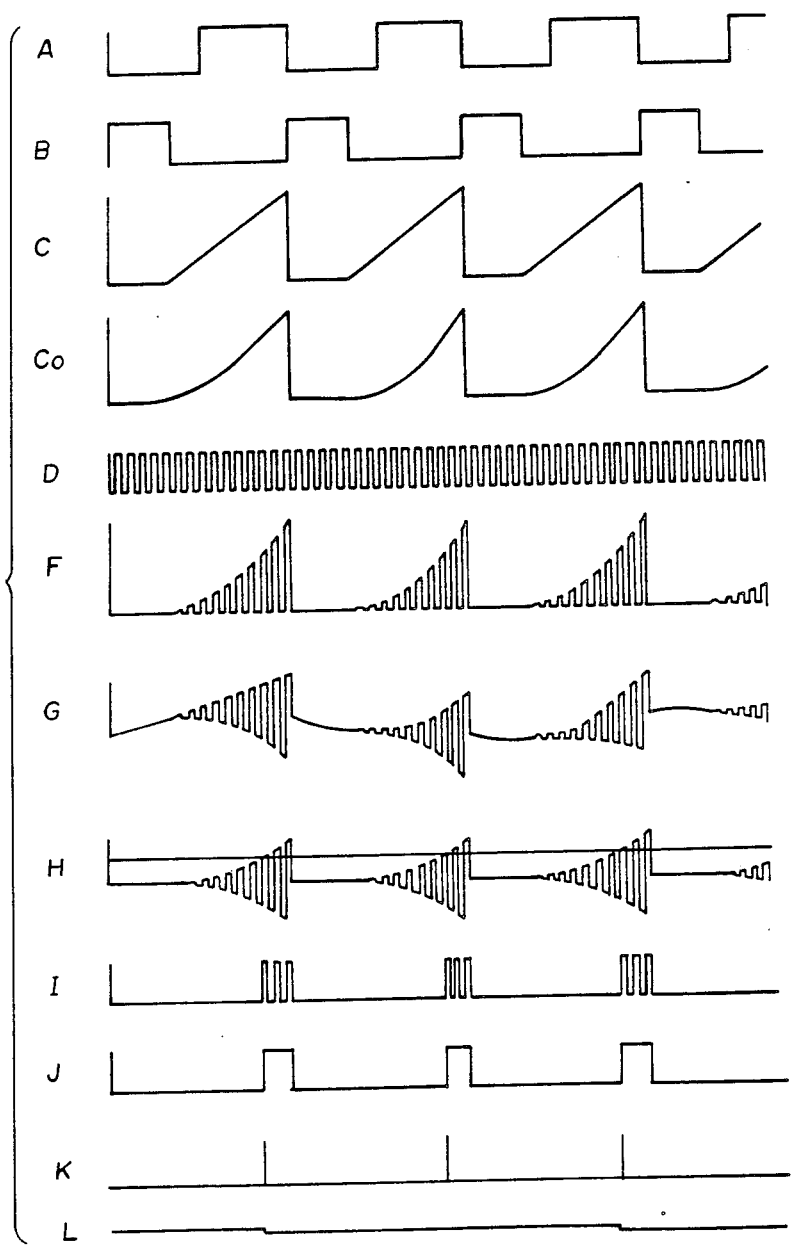
FIG. 2 is a timing chart of electric signals in the range finder as shown in FIG. 1.

The range finder has a capacitor 3 and a transistor 4 for producing a sawtooth wave, and an operational amplifier 5 for producing an output as indicated by C in FIG. 2. An operational amplifier 6 produces an output applied as a base voltage to a transistor 6a. Thus, a capacitor 7c is charged through the transistor 6a with a current as indicated by C in FIG. 2. Since the voltage charged across the capacitor 7c is of a waveform obtained by integrating the current C in FIG. 2, the voltage is proportional to the square of the current and is applied from the capacitor 7c to an operational amplifier 8, which then produces an output applied betewen the base and emitter of a transistor 8a. Therefore, a current flowing through the transistor 8a into a light-emitting diode 9 has a time-dependent waveform as indicated by Co in FIG. 2. A transistor 7b is rendered conductive by a base current supplied through an inverter 7a to discharge the capacitor 7c.

A high-frequency output, as indicated by D in FIG. 2, from an oscillator 10 is applied to the base of a transistor 10a. The current flowing through the light-emitting diode 9 is modulated by the transistor 10a into a waveform as indicated by F in FIG. 2.

The light-emitting diode 9 emits modulated infrared radiation which is converged by a lens 9a and oriented in the direction of the arrow M. A reflected beam of scattered light from an object falls on a photodiode 11 through a lens 11a in the direction of the arrow N. An electric signal generated by the photodiode 11 in proportion to the illuminance of the light falling on the photodiode 11 is amplified by an operational amplifier 12, which produces an output as indicated by G in FIG. 2. The output from the operational amplifier 12 is applied to a filter capacitor 12a which produces an output as indicated by H in FIG. 2. An operational amplifier 13 serving as an analog comparator is supplied with a reference voltage from a reference voltage source 14. When the illuminance of the photodiode 11 reaches a preset value, a detected signal is applied by the operational amplifier 13 to a flip-flop 15 to set the latter, and an output therefrom is applied to an analog switch 16 through an operational amplifier 15a. The analog switch 16, an operational amplifier 17, and a capacitor 17b jointly serve as a sample-and-hold circuit. The operational amplifier 13, the flip-flop 15, the operational amplifier 15a, and the operational amplifier 17 produce outputs as indicated by I, J, K, L, respectively, in FIG. 2. An output from a terminal 17a serves as information indicative of the distance up to the object.

Figure 3A:
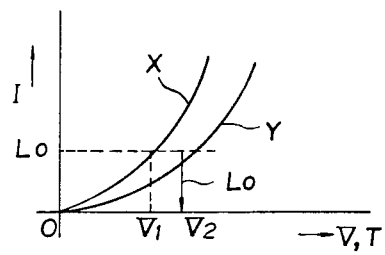
FIGS. 3a and 3b are graphs showing the relationship between the intensity of light received by a photodetector and time.
Figure 3B:
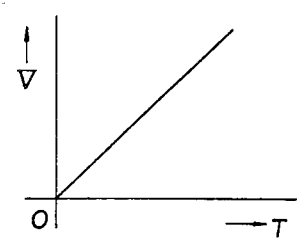

The graph of FIG. 3a has a horizontal axis representing the voltage at the terminal 17a. Since the voltage at the terminal 17a increases linearly with time as shown in FIG. 3b, the voltage at the terminal 17a may be regarded as a time base. The vertical axis of the graph of FIG. 3a is indicative of the illuminance L of the photodidode 11, which is proportional to the current I flowing through the light-emitting diode 9. The larger the distance up to the object, the smaller the illuminance of the photodiode 11, that is, the input signal to the amplifier 12 in FIG. 1, becomes in inverse proportion to the square of the distance to the object. Let distances to an object be $r_1$, $r_2$ and a preset illuminance of the photodiode 11 be Lo, and the terminal 17a produces voltages $v_1$, $v_2$ at the illuminance Lo when the object is at the distances $r_1$, $r_2$, respectively. Curves X, Y are indicative of illuminances of the photodiode 11 at the time the object is placed at the distances $r_1$, $r_2$, respectively ($r_2 > r_1$).

The illuminance L is given by:

$$L = E/r^2$$

where r is the distance to the object and E the luminance on the object surface.

Since the luminance E increases in proportion to the square of the time T or the voltage V, it is expressed by:

$$E = K_1 T^2 \text{ or } E = K_2 V^2$$

Therefore, the first equation is rewritten as:

$$Lo = K_2 V_2^2 / r_2^2 = K_2 V_1^2 / r_1^2, \text{ or}$$

$$Lo = K_2 T_2^2 / r_2^2 = K_2 T_1^2 / r_1^2$$

Accordingly, the time up to a point where the preset illuminance Lo intersects the curves is proportional to the distance to the object, or to the output voltage from the terminal 17a.

The signal A shown in FIG. 2 has a frequency in the range of from 100 to 1000 Hz, and the signal D in the range of from 10 to 100 kHz. Since the emitted infrared radiation is modulated as described above, influences due to other infrared radiations such as those in sunlight can be removed.

Figure 4:
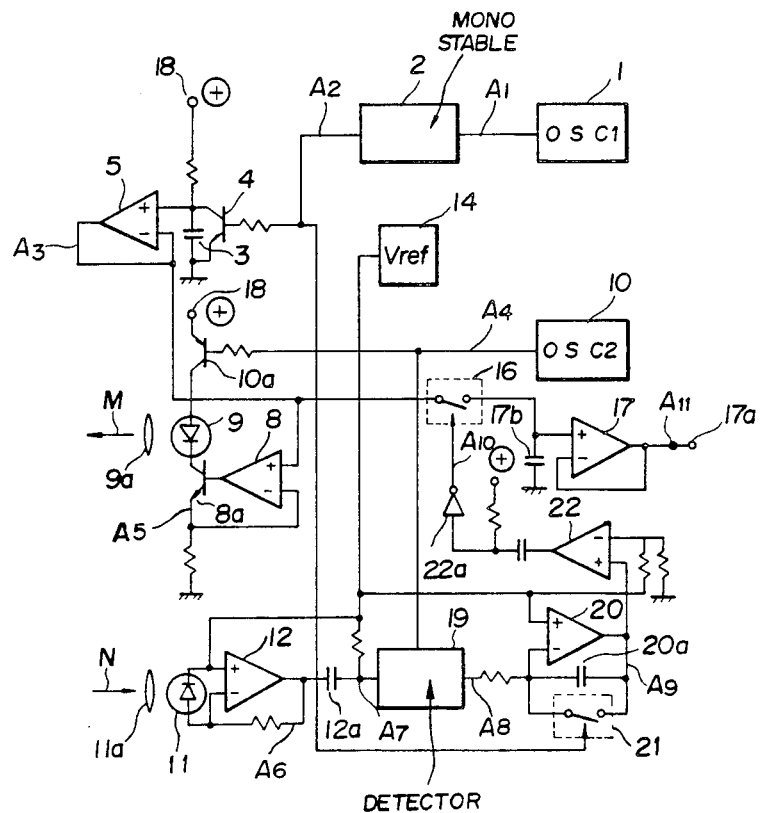
FIG. 4 is a circuit diagram of a range finder according to another embodiment of the present invention.

FIG. 4 shows a range finder in which the energy of a reflected light wave is utilized as distance information.

Where the luminuous intensity of light emitted from the light-emitting diode increases linearly, the illuminance of light falling on the photodiode is expressed by $K_1 Lo/r^2$ where $K_1$ is the reflectivity of the object, Lo is the luminous intensity, and r is the distance to the object. Since Lo inreases lineraly with time, the illuminance of the received light is indicated by $K_1 K_2 t/r^2$ where t is the time and $K_2$ is a proportionality constant. The output from the photodetector amplifier is also proportional to $t/r^2$. An integral of the signal $t/r^2$ is proportional to $t^2/r^2$, and when it reaches a preset value, $t^2/r^2 = $ constant. Therefore, the time t required until the preset value is reached after infrared radiation has started being emitted is proportional to r. The details of the foregoing will be described with reference to the embodiment of FIG. 4.

Figure 5:
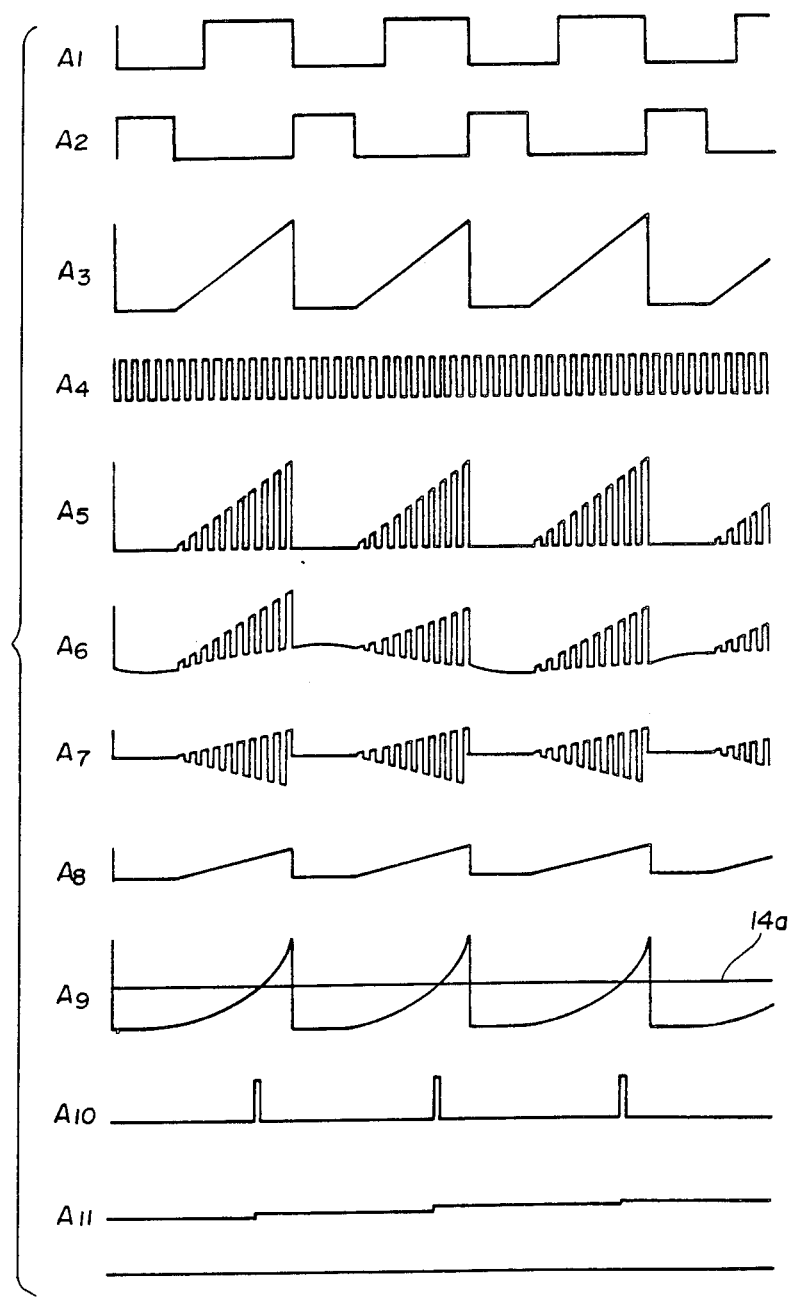
FIG. 5 is a timing chart of electric signals in the range finder as illustrated in FIG. 4.

The voltage waveforms indicated by $A_1$, $A_2$, ... in FIG. 4 are shown by the same reference characters in FIG. 5.

A sawtooth generator composed of an oscillator 1, a monostable multivibrator 2, a transistor 4, a capacitor 3, and an operational amplifier 5 operates in the same manner as that of the sawtooth generator shown in FIG. 1. The operational amplifier 5 produces a sawtooth output as indicated by $A_3$ in FIG. 5.

A transistor 8a and an operational amplifier 8 operate in the same manner as that of those shown in FIG. 1.

Since the output of the operational amplifier 5 is applied to a +terminal of the operational amplifier 8, a light-emitting diode 9 is energized in the pattern of a sawtooth waveform.

An output of a high-frequency oscillator 10 (as indicated by $A_4$ in FIG. 5) is controlled in the saturation region of a transistor 10a. The current flowing through the light-emitting diode 9 and a light beam emitted thereby are modulated as indicated by $A_5$ in FIG. 5.

A photodiode 11 produces an output proportional to the illuminance of light falling thereon and amplified by an operational amplifier 12 which generates an output as indicated by $A_6$ in FIG. 5. A filter capacitor 12a issues an output having a waveform as indicated by $A_7$ in FIG. 5. A detector 19 corresponds to an analog switch and produces a detected output as indicated by $A_8$ in FIG. 5. Therefore, the detected output is separated from external noise, producing only a desired signal output.

The output from the detector 19 is integrated with respect to time by an operational amplifier 20 and a capacitor 20a. An analog switch 21 is closed by an output from the monostable multivibrator 2 to discharge the capacitor 20a for the duration of a pulse shown in FIG. 5 at $A_2$.

The output from the operational amplifier 20 is proportional to the luminous intensity (which may be regarded as the energy of received light) as indicated by $A_9$ in FIG. 5.

A rising edge of the sawtooth waveform of $A_8$ is proportional to $t/r^2$, and an integral thereof is proportional to $t^2/r^2$ as indicated by a rising edge of a waveform $A_9$ in FIG. 5.

An operational amplifier 22 compares the rising curve of the signal $A_9$ with a comparison level established from a reference voltage from a reference voltage source 14 to produce a detected signal, the comparison level being represented by a straight line 14a in $A_9$. The operational amplifier 22 produces an output at each position where the comparison level 14a intersects the signal $A_9$, and the output form the operational amplifier 22 is converted by a differentiating circuit and an inverter 22a into a hold pulse as indicated b $A_{10}$ in FIG. 5. The hold pulse closes an analog switch 16 which produces an output that is held by a sample-and-hold circuit composed of an operational amplifier 17 and a capacitor 17b.

The output from the analog switch 16 is indicative of the output from the operational amplifier 5, that is, the peak value of a linear rising edge of the sawtooth waveform. The peak value is a voltage proportional to the time required until the integrated output from the operational amplifier 20 reaches a prescribed value after infrared radiation has started being emitted. Therefore, the peak value is indicative of the time 5 until $t^2/r^2$ becomes a constant value, so that a terminal 17a produces an output voltage as indicated by $A_{11}$ in FIG. 5 proportional to the distance to the object.

An arrangement will now be described in which the distance as measured by the range finders as described above based on the illuminance or luminous intensity of received light can be perceived by a blind person.

Figure 6:
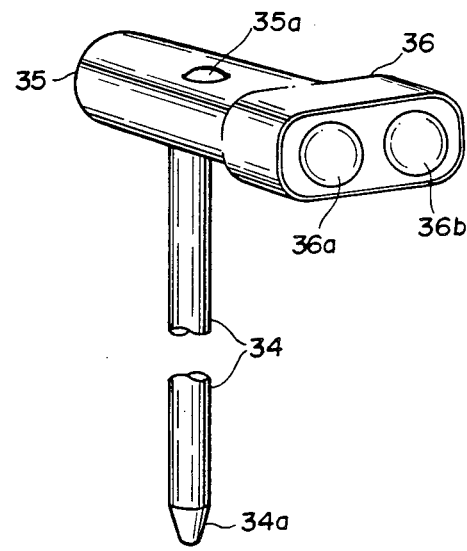
FIG. 6 is a perspective view of a walking stick for the blind which incorporates a range finder and a vibrator.
Figure 7:
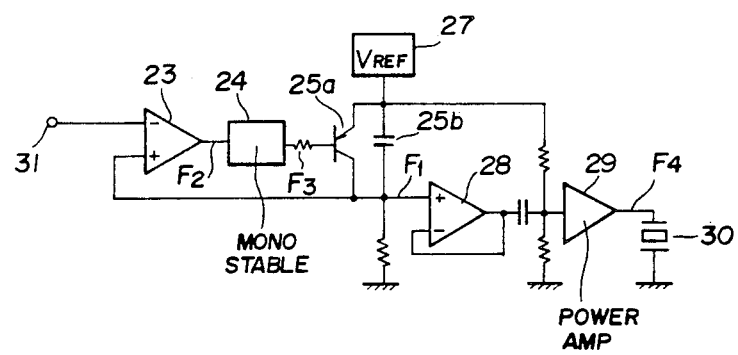
FIG. 7 is a circuit diagram of an electric circuit arrangement for convering an electric signal from a range finder into vibrations of a vibrator.

FIG. 6 shows a walking stick for use by a blind person. The walking stick, designated 34, supports on its upper end a handle 35 with a casing 36 mounted on a front end thereof. The casing 36 contains the range finder circuit as shown in FIGS. 1 or 4, and a circuit and a battery (described later) as shown in FIG. 7. The casing 36 supports on its front face a lens 36a for irradiating a beam of infrared radiation emitted from the light-emitting diode and a lens 36b for efficiently detecting scattered infrared radiation reflected from an object. The handle 35 has a vibrator plate 35a mounted on an upper surface thereof so that the vibrator plate 35a will be contacted by a palm or fingertip of the user when the handle 35 is gripped by the user. While the blind person is walking with the walking stick 34, the distance up to an object lying in the direction in which the range finder faces is transmitted or perceived as vibrations of the vibration plate 35a. The amplitude of the vibrations is greater as the distance is smaller, and is smaller as the distance is greater. Since the vibrations can be sensed more clearly by the skin as the frequency thereof is lower, the amplitude of the vibrations may be fixed and the frequency may be increased as the distance to the object is increased. Alternatively, the amplitude may be higher and the frequency may be lower as the distance gets smaller, and the amplitude may be smaller and the frequency may be higher as the distance gets larger.

Figure 8:
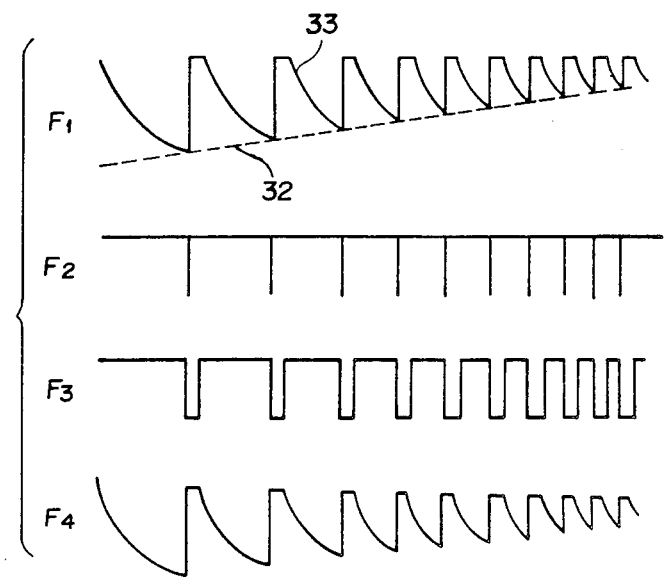
FIG. 8 is a timing chart of electric signals in the electric circuit arrangement shown in FIG. 7.

One means for producing vibrations dependent on the distance to an object is shown in FIG. 7. In FIG. 7, a capacitor 25b is charged by a reference voltage source 27, and the output from the terminal 17a (FIGS. 1 or 4) is applied to a terminal 31. The input to the terminal 31 is in the form of a voltage proportional to the distance to the object. When a voltage indicated by $F_1$ (also in FIG. 8) is lowered until it is equal to the input to the terminal 31, an electric signal ($F_2$ in FIG. 8) is applied from an analog comparator 23 to a monostable multivibrator 24 which produces a pulse of a certain duration ($F_3$ in FIG. 8).

The electric signal form the monostable multivibrator 24 is applied to the base of a transistor 25a to render the latter conductive, thus discharging a capacitor 25b according to the waveform $F_1$. Thus, the capacitor 25b serves as an oscillator which is repeatedly charged and discharged. The smaller the input voltage applied to the terminal 31, that is, the shorter the distance to the object, the lower the oscillation frequency and the greater the amplitude. The input voltage to the terminal 31 is indicated by the dotted line 32 in FIG. 8 at $F_1$. The pulses of $F_2$ are generated at points where the line 32 intersects a curve 33. The electric signal 33 is applied to an operational amplifier 28 which issues an output to a power amplifier 29 that produces an output as indicated by $F_4$ in FIG. 8 applied to a vibrator 30.

The vibrator, which is denoted by 35a in FIG. 6 and 30 in FIG. 7, may comprise a vibrator used in a voice-coil-type loudspeaker, a piezoelectric loudspeaker or the like.

Figure 9:
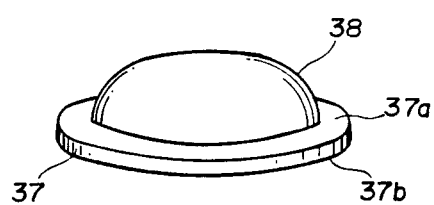
FIG. 9 is a perspective view of a piezoelectric loudspeaker having a projection.
Figure 10:
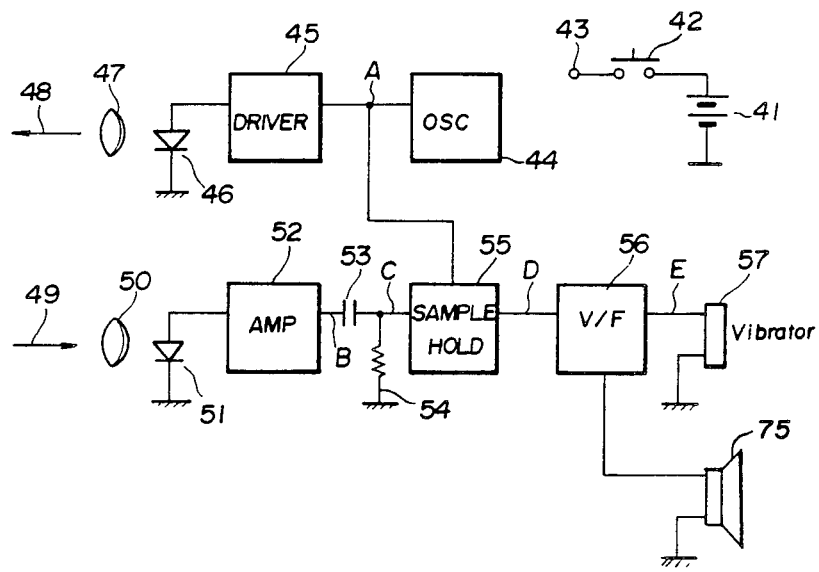
FIG. 10 is a circuit diagram of a range finder according to still another embodiment of the present invention.

FIG. 9 illustrates an arrangement in which a vibrator 37 has opposite surfaces 37a, 37b, and a rounded projection 38 is attached to the surface 37a of the vibrator 37. The rounded projection 38 serves to transmit vibrations more easily to the palm or fingertip of the use. The projection 38 may be kept in contact with the skin of other portions of the body for tranmitting vibrations to the user.

As described above, the blind person guide device of the invention allows a blind person to conform the safety at the feet with the walking stick while at the same time perceiving the presence, distance, and bearing of an obstacle placed at a distance of about 10 m with the range finder incorporated in the walking stick.

A range finder according to another embodiment will be described with reference to FIGS. 11 through 14. The range finder emits infrared radiation to detect an object within a range which is about 10 m from the range finder.

A beam of infrared radiation is emitted by a light-emitting element toward an object, and a beam of infrared radiation is reflected by the object and received by a photodetector. Since the intensity of the received indrared radition is inversely proportional to the distance to the object, the distance can be measured by processing the signal indicative of the intensity of the received indrared radition. The intensity of the detected radiation affects the reflectivity of the object which reflect the emitted radiation. Since infrared radiation having a wavelength of about 1 micron produces smaller differences in reflectivity of various objects than visible light, infrared radiation can cause no practical problem if used by devices for assisting blind persons in walking safely. Since the beam of radiation is emitted, the range finder has an increased resolution in the direction in which the distance is measured.

The embodiment of FIGS. 10 through 13 will hereinafter be described. When a power supply switch 42 is closed, a battery 41 supplied a current through a terminal 43 to an oscillator 44, a driver 45, an amplifier 52, a sample-and-hold circuit 55, and a voltage frequency converter 56. The oscillator 44 produces an output A as indicated by A in FIG. 11, the output A being a pulse signal having a repetition frequency of 100 Hz and a pulse duration of about 10 microseconds. The pulse signal is applied to the driver 45 which supplies a current to a light-emitting diode 46. Assuming that the supplied current has a peak value of 1 ampere, an average consumed current is about 1 milliampere. Infrared radiation emitted from the light-emitting diode 46 is changed by a lens 47 into a beam of parallel rays, which is radiated on an object in the direction of the arrow 48. Reflected radiation from the object in the direction of the arrow 49 is focused by a lens 50 to fall on a photodiode 51. The photodiode 51 generates a current proportional to the intensity of detected light, the current being amplified by the amplifier 52 and converted thereby into a voltage signal. Since disturbance light such as sunlight or illumination light also enters the photodiode 51 at this time, the amplifier 52 produces an output B which is indicated by B in FIG. 11.

Figure 11:
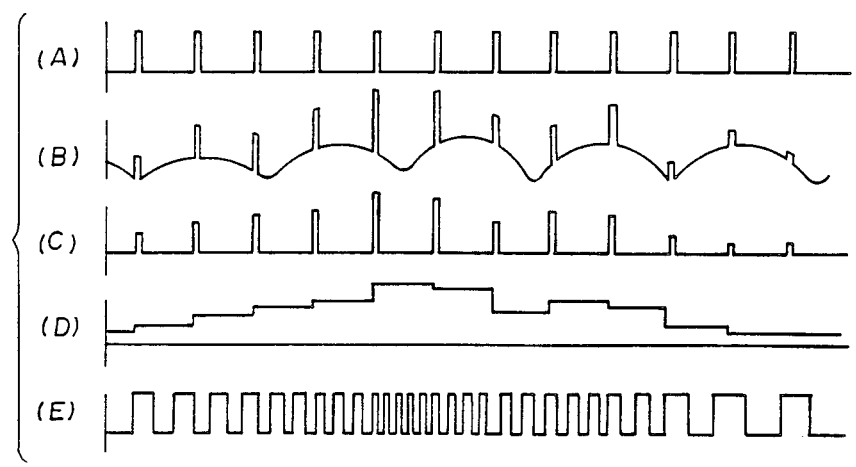
FIG. 11 is a timing chart showing electric signals in the range finder of FIG. 10.
Figure 1:
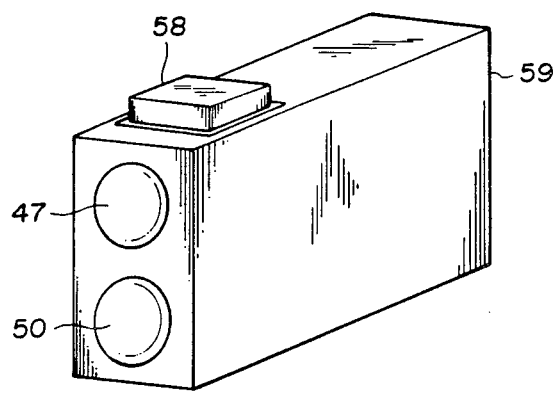
Figure 13:
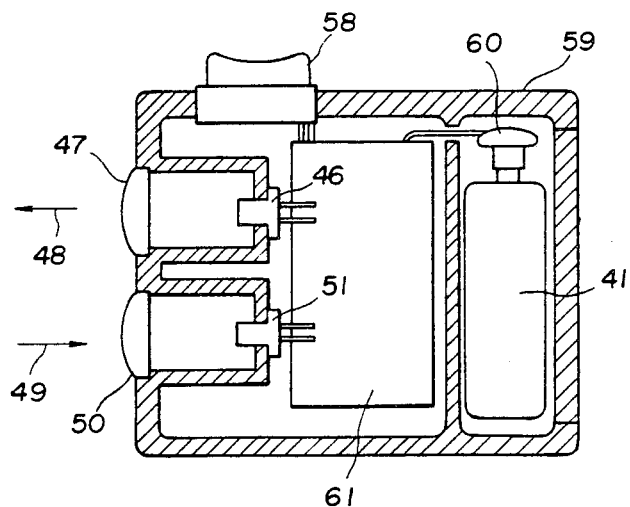

A capacitor 53 and a resistor 54 jointly serve as a bypass filter which removes the influence of the disturbance light and produces a pulse signal C which is indicated by C in FIG. 11. The pulse signal C has a peak value which is inversely proportional to the square of the distance to the object. The signal C from the bypass filter is applied to the sample-and-hold circuit 55 in which it is sampled in synchronism with the output signal A from the oscillator 44. An output D from the sample-and-hold circuit 55 is indicated by D in FIG. 11. The signal D is applied to the voltage frequency converter 56 to enable the latter to oscillate at a frequency (below 1 kHz) proportional to the applied voltage. An output signal E (FIGS. 10 and 11) from the voltage frequency oscillator 56 is applied to a vibrator 57. Therefore, the vibrator 57 is vibrated at a frequency inversely proportional to the square of the distance to the object.

Figure 14:
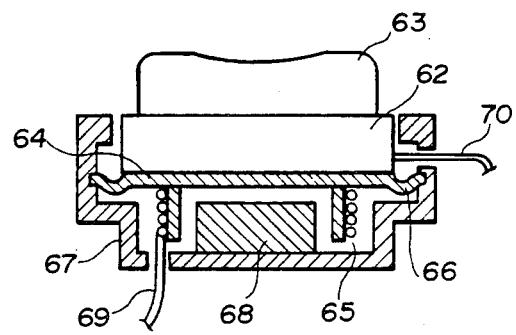
FIGS. 14 and 15 are cross-sectional and side elevational views of different integral constructions of a power supply switch and a vibrator.
Figure 15:
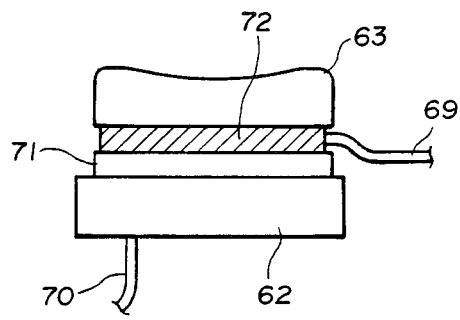

The power supply switch 42 and the vibrator 57 may be incoporated integrally in a pushbutton switch as shown in FIGS. 14 and 15.

As shown in FIG. 14, a pushbutton switch has a casing 62 and a cap 63. The pushbutton switch is turned on only when the cap 63 is depressed. The casing 62 of the pushbutton switch is fixed to an upper surface of a vibrator 64 with a voice coil 65 secured to a lower surface thereof. The vibrator 64 is peripherally supported by an edge 66 in a casing 67 so that the vibrator 64 can be moved upwardly and downwardly in the casing 67. A magnet 68 is fixed to the bottom of the casing 67 and positioned in the voice coil 65. Therefore, when a low-frequency current is passed through the the voice coil 65, it is vibrated vertically at the same frequency as that of the low-frequency current, and the vibrations are transmitted to the vibrator 64, the casing 62, and the cap 63.

FIG. 15 illustrates another embodiment. Idential parts in FIG. 15 are denoted by identical reference numerals in FIG. 14. A piezoelectric element 72 capable of vibrating in a transverse direction is fixed to an upper surface of a presser 71, with a cap 63 mounted on an upper surface of the piezoelectric element 72. When a low-frequency voltage is applied to the piezoelectric element 72, it is vibrated vertically at the same frequency as that of the low-frequency voltage to transmit vibrations to the cap 63.

The following is a description of another embodiment. The V/F converter 56 is connected to an electroacoustic transducer 75 such as an earphone or loudspeaker. The output signal E (FIGS. 10–11) from the V/F converter is applied to the transducer 75. The oscillator i.e. V/F converter 56 is arranged to produce electric vibrations having a frequency which is higher as the distance to the object is shorter.

The acoustic sound of a frequency dependent on the distance to the object are transmitted to the ears of the blind person as aid for walking safely.

With the arrangement of the present invention, when a blind person carrying the guide device of the invention wishes to know the distance up to an obstacle located in a direction in which the guide device faces, the guide device is held by hand and the vibrator is depressed with a fingertip, whereupon vibrations of a frequency dependent on the distance to the object are transmitted to the blind person. If no distance information is needed, then the vibrator should be released to turn off the power supply at the same time.

Thus, there is provided in accordance with the invention a blind person guide device which has the advantage discussed above. The embodiments described are intended to be merely exemplary and those skilled in the art will be able to make variations and modifications in them without departing from the spirit and scope of the inventions. All such modifications and variations are contemplated as falling within the scape of the claims.

What is claimed is:

1. A blind person guide device comprising:
   a source for emitting a beam of pulse-shaped infrared radiation of a peak value that is limited in a forward direction;
   a photoelectric element for receiving infrared radiation reflected from an object irradiated by said beam;
   an electric circuit having means for removing an influence of a disturbance light such as sunlight or illumination light from the illuminance or received radiation on said photoelectric element by modulating said infrared radiation at an audio frequency between 100 and 1000 Hz, and means for sampling-and-holding the signal from said influence removing means, the resulting held signal corresponding to information as to a distance to the object;
   an oscillator for generating electric vibrations having a frequency and an amplitude which are dependent on the distance information produced by said electric circuit; and
   a power supply switch for energizing and de-energizing said electric circuit and said oscillator, said power supply switch having a pressor comprising a vibrator which is vibratable in response to said electric vibrations and against which a human skin can be pressed.

2. A blind person guide device according to claim 1, wherein said oscillator is arranged to produce electric vibrations having a frequency which is higher as the distance to the object is shorter.

3. A blind person guide device comprising:
   a source mounted on a front face of said device for emitting a beam of infrared radiation in a forward direction, said radiation comprising a repetition of pulses with selectively varying peak values;
   a photoelectric element mounted on said front face of the device for receiving infrared radiation reflected from an object irradiated by said beam;
   an electric circuit having means for removing an influence of distrubance light such as sunlight or illumination light by modulating said infrared radiation at an audio frequency of between 100 and 1000 Hz and comparator means for comparing the illuminance or energy of received radiation on said photoelectric element with a preset value and means for sampling and holding said peak value when said illuminance or energy of received radiation reaches said preset value, the resultant held signal corresponding to an information as to a distance to the object;
   an oscillator for generating electric vibrations having a frequency and an amplitude which are dependent on the distance information produced by said electric curcuit; and
   a vibrator vibratable in response to said electric vibrations and having a vibrating surface against which a human skin can be pressed.

4. A blind person guide device according to claim 3, wherein said oscillator is arranged to produce electric vibrations having a frequency which is higher as the distance to the object is shorter and an amplitude which is greater as the distance to the object is shorter.

5. The blind person guide device according to claim 3 further comprising a power supply switch for energizing and de-energizing said electric circuit and said oscillator, said power supply switch including said vibrator which vibrates while said power supply switch is in an "on" state.

* * * * *